US006200282B1

(12) United States Patent
Furuie et al.

(10) Patent No.: US 6,200,282 B1
(45) Date of Patent: Mar. 13, 2001

(54) MASSAGE MACHINE OF CHAIR TYPE

(75) Inventors: Yoshiya Furuie, Himeji; Yoshihiro Tanimoto, Hyogo, both of (JP)

(73) Assignee: Sanyo Electric Co., Ltd., Osaka (JP)

( * ) Notice: Subject to any disclaimer, the term of this patent is extended or adjusted under 35 U.S.C. 154(b) by 0 days.

(21) Appl. No.: 08/863,070

(22) Filed: May 23, 1997

(30) Foreign Application Priority Data

May 27, 1996 (JP) ... 8-131609
May 28, 1996 (JP) ... 8-133149

(51) Int. Cl.[7] ... A61M 7/00
(52) U.S. Cl. ... 601/98; 601/101; 601/108
(58) Field of Search ... 601/84, 97, 98, 601/99, 101, 103, 107, 108, 111, 115, 116, 134

(56) References Cited

U.S. PATENT DOCUMENTS 4,009,710 3/1977 Inada ... 128/44
4,899,403 * 2/1990 Yamasaki ... 601/99
5,020,518 * 6/1991 Spears et al. ... 601/116
5,460,598 * 10/1995 Yamasaki et al. ... 601/98
5,462,516 * 10/1995 Anderson ... 601/99

FOREIGN PATENT DOCUMENTS 94 19 742U 3/1965 (DE) .
37 12 085A 10/1987 (DE) .
3712085 * 10/1987 (DE) ... 601/99
405003899 * 1/1993 (JP) ... 601/98

* cited by examiner

*Primary Examiner*—Mickey Yu
*Assistant Examiner*—Benjamin K. Koo
(74) *Attorney, Agent, or Firm*—Armstrong, Westerman, Hattori, McLeland & Naughton

(57) ABSTRACT

The invention provides a massage machine of the chair type having contact portions for applying a pressing force concentrically or dividedly so as to massage the user with the desired intensity. The machine comprises a massage unit having a first therapeutic finger for giving tapping massage to the upper part or the upper to frontal part of the shoulder of the user, and a second therapeutic finger for giving tapping massage to the back or the back to the posterior part of the shoulder. The fingers each have a portion to be brought into contact with the user at the forward end of an arm. The arms are pivotally movable independently of each other by respective finger drive means.

5 Claims, 9 Drawing Sheets

MASSAGE MACHINE OF CHAIR TYPE

FIELD OF THE INVENTION

The present invention relates to massage units and massage machine of the chair type which comprise therapeutic fingers for massaging the affected part of the user to be treated.

BACKGROUND OF THE INVENTION

Various massage machines or devices are known for pressing or stimulating the shoulders, waist or other parts of the human body to remove stiffness. According to the type, such devices can be divided into the chair type, bed type and handy type. With respect to the mode of action on the affected part, these devices resort to finger pressure, vibrations or electrical stimulation.

FIG. 13 shows a massage machine 90 of the chair type which is especially in wide use among other massage devices. The machine 90 comprises a chair 91 for the person to be massaged (hereinafter referred to as the "user"), and a pair of therapeutic fingers 95, 95 projecting forward from the backrest 92 of the chair. Each of the finger 95 comprises an arm 93 coupled to a motor (not shown) for driving the finger, and a contact portion 94 provided at the forward end of the arm 93 and adapted to be brought into contact with the affected part of the user. When the motor is driven, the therapeutic fingers 95, 95 perform a tapping operation vertically of the machine or a lateral kneading operation to massage the user.

Although adapted to massage the posterior part of the user's shoulder and the back, the massage machine thus constructed is unable to massage the upper part or the upper to frontal part of the shoulder.

Furthermore, the massage machine continually massages a particular portion of the affected part, so that if the machine is used for a prolonged period of time, the affected part will feel painful or becomes insensitive, or the user is likely to become tired of massage.

The massage machine acts on the user by pressing the affected part from behind, so that if used continuously, the upper part of the user's body is gradually pushed forward, failing to remain in position stably. Thus, the machine is unable to produce a satisfactory massage effect.

Additionally, when the machine is used for massaging the affected part of the user, especially the back or the waist, it is impossible to alter the area of the pressing contact of the therapeutic finger contact portion 94 with the user's body. In other words, the pressing force to be applied locally by the contact portion can not be increased or decreased to give the desired intensity.

An object of the present invention is to provide a chair-type massage machine and massage unit which are adapted to give a wide variety of massage operations.

Another object of the invention is to provide a massage machine of the chair type for applying a pressing force concentrically or dividedly so as to massage the user with the desired intensity.

SUMMARY OF THE INVENTION

The present invention provides a massage machine of the chair type comprising a massage unit disposed in a backrest of a massage chair. The massage unit has a pair of therapeutic fingers arranged one above the other and projecting forward from the backrest. Each of the fingers comprises an arm, and a contact portion provided at a forward end of the arm. The arms are coupled each at a base end thereof to respective finger drive means to render the therapeutic fingers individually pivotally movable in a vertical plane. The contact portion at the forward end of the upper therapeutic finger is movable to a position permitting the contact portion to reach the upper part or the upper to frontal part of the shoulder of the user as seated in the chair.

The invention further provides a massage unit comprising a first therapeutic finger for giving tapping massage to the upper part or the upper part to frontal part of the shoulder of the user, and a second therapeutic finger for giving tapping massage to the back or the back to the posterior part of the shoulder of the user. Each of the fingers comprises an arm and a contact portion provided at a forward end of the arm. The arms are coupled to respective finger drive means and pivotally moved and stopped by these means independently of each other.

The first finger drive means and the second finger drive means can be a first finger drive motor and a second finger drive motor, respectively, which are operable independently of each other. Tapping massage can be given to the affected part of the user by one of the first and second therapeutic fingers by holding one of the first and second finger drive motors at rest with the contact portion in contact with the affected part and driving the other finger drive motor alone forward and reversely repeatedly.

The invention further provides a massage machine of the chair type comprising two massage units arranged side by side in a backrest of a chair, each of the massage units comprising a pair of upper and lower therapeutic fingers each including an arm projecting forward from the backrest and a contact portion provided at a forward end of the arm for giving massage in contact with the affected part of the user. Each massage unit further comprises a finger drive assembly for moving the upper and lower contact portions toward and away from each other. The two massage units are coupled to a drive portion for moving the units sideways toward and away from each other. Thus, the massage units can be reciprocatingly moved sideways with the upper and lower contact portions held in contact with each other or spaced apart.

The invention further provides a massage machine of the chair type comprising a massage unit in a backrest of a chair, the massage unit comprising a pair of upper and lower therapeutic fingers each including an arm projecting forward from the backrest and a contact portion provided at a forward end of the arm for giving massage in contact with the affected part of the user, the massage unit further comprising a finger drive assembly coupled to base ends of the arms for moving the upper and lower contact portions toward and away from each other. The massage unit is coupled to a lift mechanism disposed in the backrest and movable upward and downward inside the backrest. The lift mechanism moves the massage unit upward and downward with the contact portions held in contact with each other or spaced apart by the finger drive assembly.

DESCRIPTION OF THE PREFERRED EMBODIMENTS

Embodiment 1

An embodiment of the invention will be described. In the following description, the term "front"refers to the direction toward which the user 15 sitting in a chair 14 faces, i.e., the direction of arrow F in FIG. 1.

Figure 1:
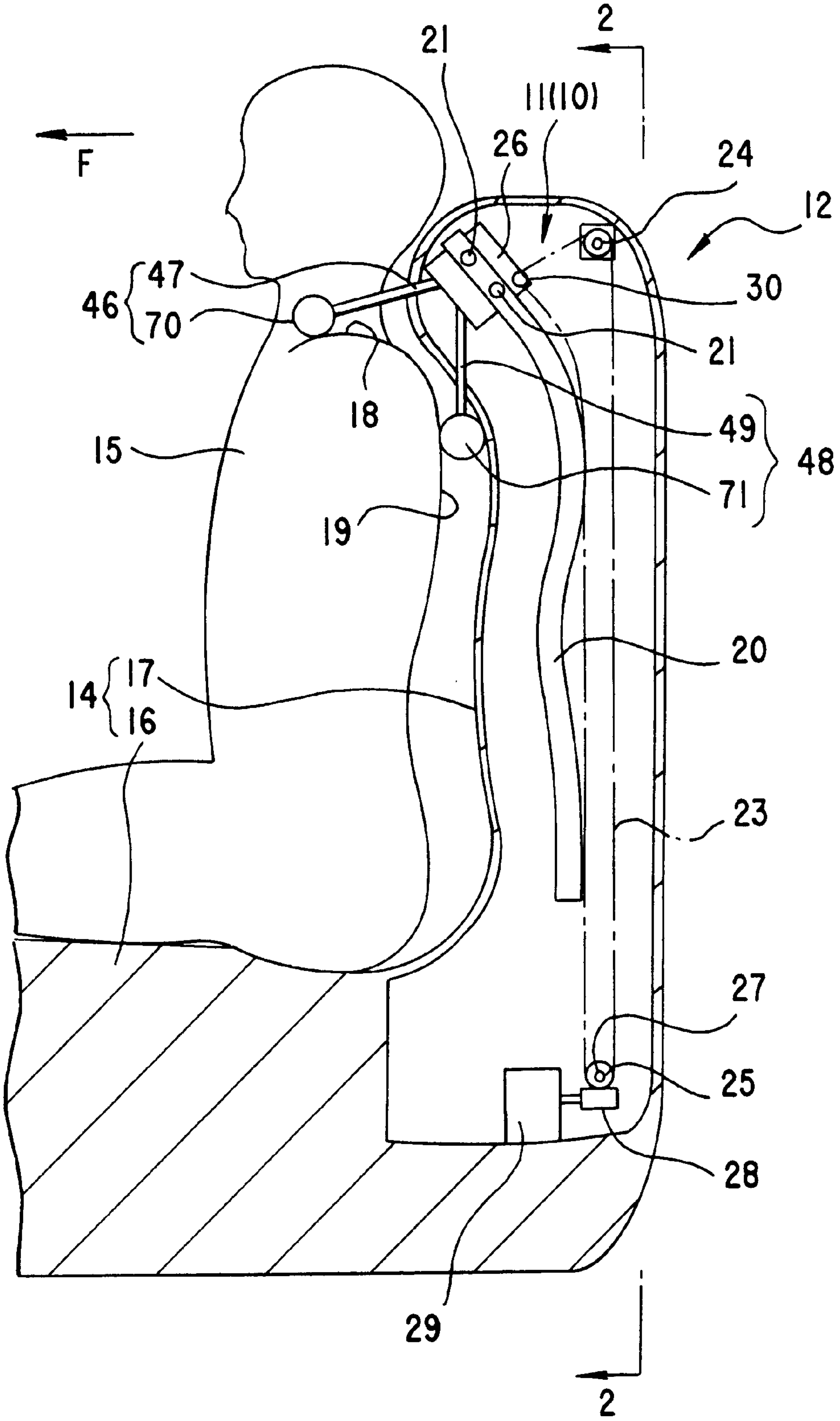
FIG. 1 is a sectional view showing a chair-type massage machine of the invention.

With reference to FIG. 1, a massage machine 12 has the above-mentioned chair 14 which comprises a seat 16 for the user 15, and a backrest 17 extending upward from the rear end of the seat 16. The backrest 17 is provided with a pair of massage units 10, 11 which are movable upward and downward and also movable laterally toward and away from each other.

First, a description will be given of a lift mechanism for moving the massage units 10, 11 upward and downward.

Figure 2:
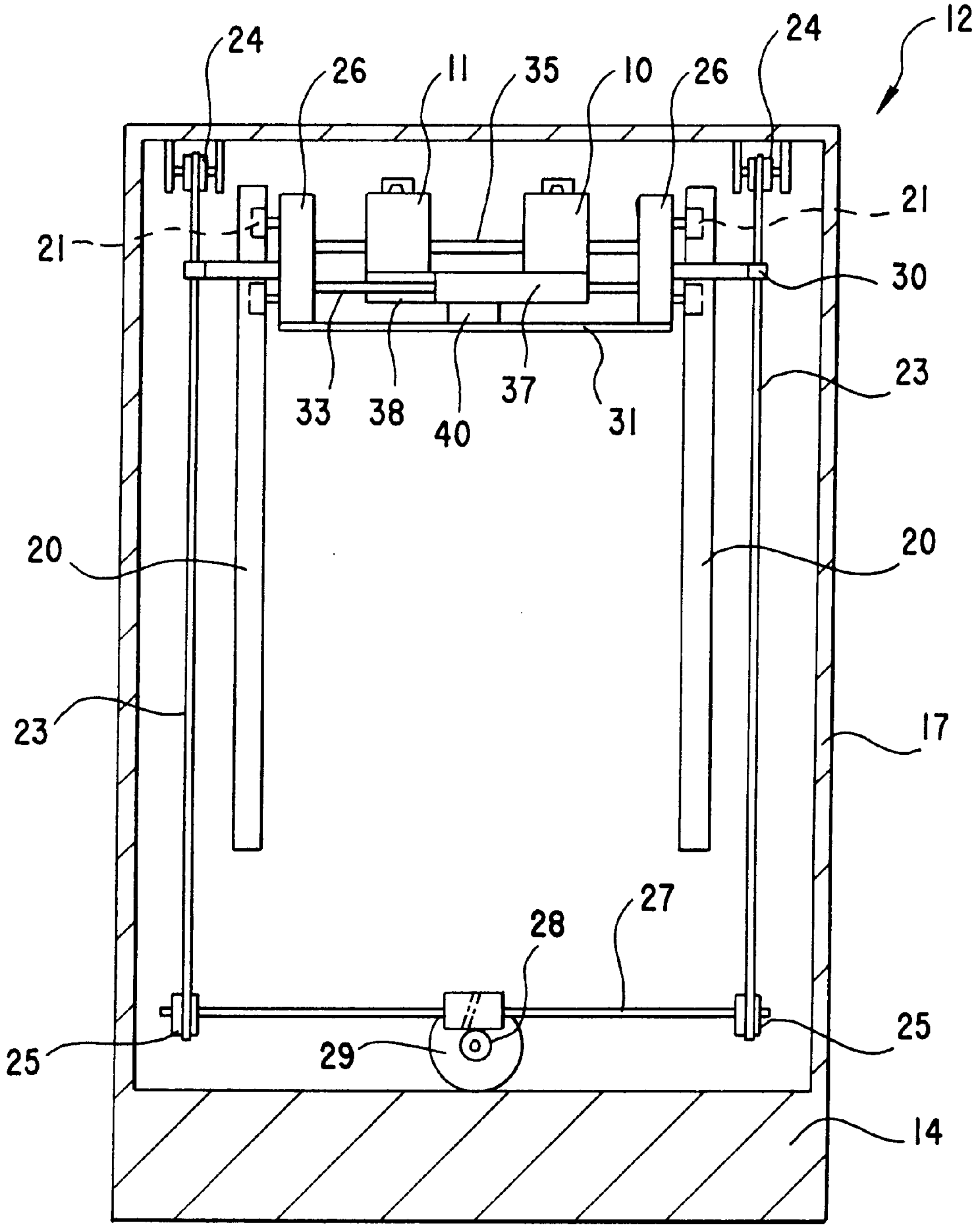
FIG. 2 is a view in section taken along the line A—A in FIG. 1 and showing the machine as it is seen in the direction of the arrows.

As shown in FIGS. 1 and 2, the backrest 17 of the chair 14 has in its interior a pair of guide rails 20, 20 extending vertical in parallel to each other and bent in conformity with the back 19 (more specifically, the backbone) of the user 15. The upper end of each guide rail 20 is bent forward so that an upper contact portion 70 of each of the massage units 10, 11 to be described below will come into contact with the top portion or the top to front portion of the shoulder 18 of the user 15. The guide rail 20 has fitted thereto guide rollers 21, 21 for guiding the massage unit for upward and downward movement. Thus, the massage units 10, 11 are movable upward and downward along the respective guide rails 20, 20.

Endless chains 23, 23 for moving the respective massage units 10, 11 are arranged alongside of and to the rear of the respective guide rails 20, 20. Each chain 23 is in engagement with sprockets 24, 25 rotatably provided within the backrest 17 respectively at an upper portion and lower portion thereof. The chain 23 has a portion connected to a support block 26, which will be described later, for holding the massage unit.

A shaft 27 for the lower sprockets 25 is coupled to a chain drive motor 29 by means of a reduction gear mechanism 28. The massage units 10, 11 are movable upward or downward along the guide rails 20, 20 by the forward or reverse rotation of the motor 29.

The massage units 10, 11 will be described next.

The units 10, 11 are provided at right and left, respectively, so as to massage the right side and left side of the body upper portion of the user 15. These massage units 10, 11 are movable toward and away from each other as arranged between the support blocks 26, 26 which are spaced apart by a predetermined distance.

The guide rollers 21, 21 fitting in the guide rail 20 are rotatably mounted on the outer side of each support block 26. The chain 23 has one portion fixed to a chain holder 30 projecting from the support block 26.

Figure 3:
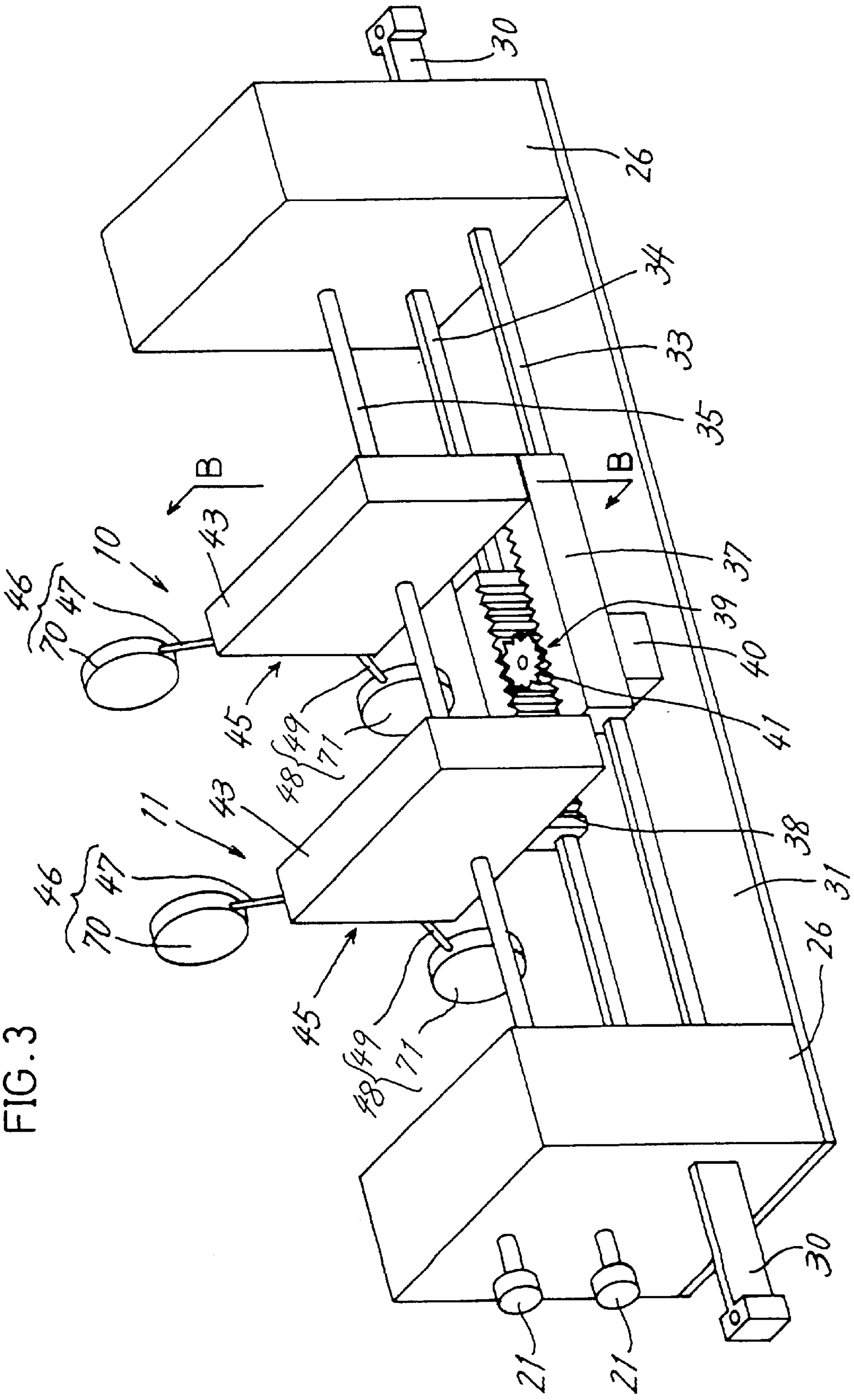
FIG. 3 is a perspective view of massage units as they are seen from behind.

The support blocks 26, 26 have their bottoms fixed to a holding plate 31 for holding the blocks spaced apart by the predetermined distance. As shown in FIG. 3, two guide bars 33, 34 and a support rod 35 arranged in parallel have their opposite ends fixed to and supported by the blocks 26, 26.

The two guide bars 33, 34 are arranged in a horizontal plane. The rear guide bar 33 will hereinafter be referred to as the "guide bar for the right," and the front guide bar 34 as the "guide bar for the left." The support rod 35 is positioned to the front of and above the guide bar 34 for the left.

The guide bars 33, 34 for the right and left have slidably fitted thereto a right rack 37 and a left rack 38, respectively, with their toothed faces opposed to each other. A motor 40 for moving the units 10, 11 toward or away from each other is mounted on the holding plate 31 and has a pinion 41 meshing with teeth of both the racks 37, 38 at the same time, thereby to provide a drive portion 39 for moving the units 10, 11 sideways toward and away from each other.

When driven forward, the motor 40 moves the two racks 37, 38 toward the center. When rotated reversely, the motor 40 moves the right rack 37 rightward, and the left rack 38 leftward.

The right rack 37 carries the massage unit 10 for massaging the right side of upper half of the user's body. The left rack 38 is provided with the massage unit 11 for massaging the left side of upper half of the body. Although only the massage unit 10 for the right side will be described below, the massage unit 11 for the left side has the same construction as the unit 10.

Figure 4:
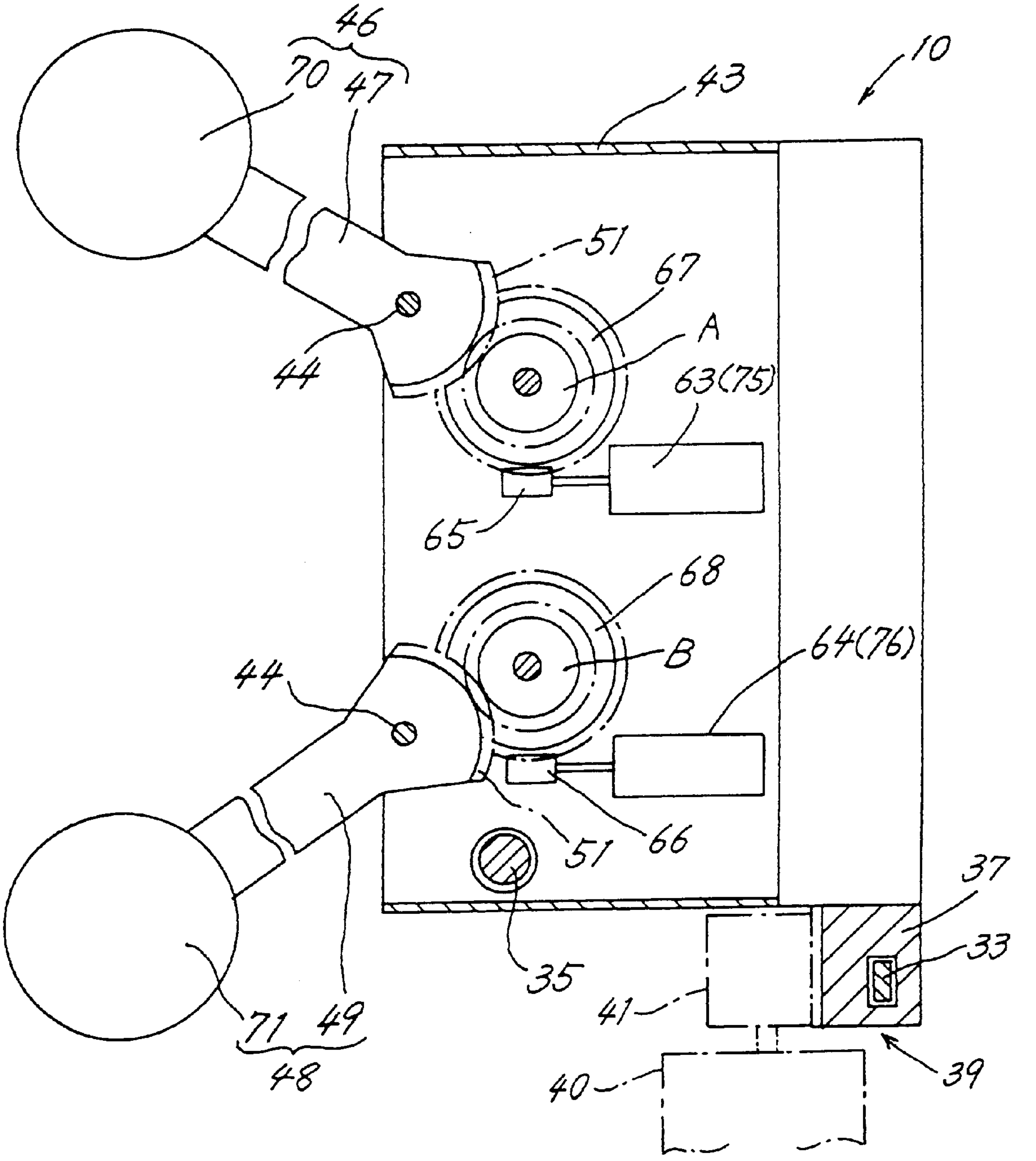
FIG. 4 is a view in section taken along the line B—B in FIG. 3 and showing the massage unit.

With reference to FIG. 4, the massage unit 10 for massaging the right side of upper half of the body comprises a casing 43 secured to the right rack 37, and a pair of upper and lower therapeutic fingers 46, 48 supported by the casing 43.

The casing 43 is secured at its bottom to the right rack 37. The support rod 35 slidably extends through the casing 43 at a front portion thereof.

As shown in FIG. 4, each of the therapeutic fingers 46, 48 comprises a contact portion 70 (71) in the form of a disk of large thickness for massaging the affected part of the user 15 in contact therewith, and an arm 47 (49) having the contact portion at its forward end. The arms 47, 49 of the pair of fingers 46, 48 are positioned one above the other with a specified opening angle formed therebetween and supported by respective pivots 44, 44 in the casing 43 of the unit 10 so as to be pivotally movable in a vertical plane. The forward ends of the arms 47, 49 project from a front opening of the casing 43 and each have a base end formed with a sector gear 51 which is rotatable about the pivot.

The casing 43 houses finger drive means 75, 76 for pivotally moving the respective therapeutic fingers 46, 48 in a vertical plane. With the present embodiment, two motors 63, 64 are used as the finger drive means 75, 76 for individually driving the fingers 46, 48 independently of each other. The drive shafts of the finger drive motors 63, 64 carry respective worms 65, 66 which are in mesh with respective worm wheels 67, 68 supported by the casing 43 with shafts. The worm wheel 67 is integral with an intermediate gear A, which is in mesh with the sector gear 51 of the first arm 47 above the other arm. The lower worm wheel 68 is integral with an intermediate gear B, which is in mesh with the sector gear 51 of the lower second arm 49.

When the first finger drive motor 63 and the second finger drive motor 64 are driven for forward and reverse rotation by changing-over, the therapeutic fingers 46, 48 are pivotally moved about the respective pivots by means of the gears toward or away from each other.

The left massage unit 11 is similar to the right massage unit 10 in construction and has a casing 43 having its bottom secured to the upper side of the left rack 38.

The massage machine 12 of the foregoing construction is adapted to perform various massage operations as shown in FIGS. 5 to 9 by combinations of the forward or reverse rotation of the first finger drive motor 63 and the second finger drive motor 64, stopping of the motor and the variation of the drive period thereof.

Prior to the following massage operations, the massage units 10, 11 are adjusted in position by driving the chain motor 29 and the motor 40 so that the contact portions 70 of the first fingers 46 each bear on the upper part or the upper to front part of the user's shoulder 18, with the contact portions of the second fingers 48 positioned for contact with the back 19 of the user 15.

Various massage operations are performed in this state. With reference to FIGS. 5 to 9, (a) shows the phase of the contact portion 70 of the first finger 46, (b) shows the phase of the contact portion 71 of the second finger 48, and zero represents the contact of the contact portion 70 or 71 with the affected part. Further with respect to the contact portion 70 of each first therapeutic finger 46, the plus side represents the movement of the contact portion 70 toward a shoulder pressing direction, and the minus side represents the movement of the contact portion 70 in a direction away from the shoulder 18. In connection with the contact portion 71 of each second therapeutic finger 48, the plus side represents the movement of the contact portion 71 toward a back pressing direction, and the minus side represents the movement of the contact portion 71 in a direction away from the back 19. Massage operations will now be described.

Figure 5:
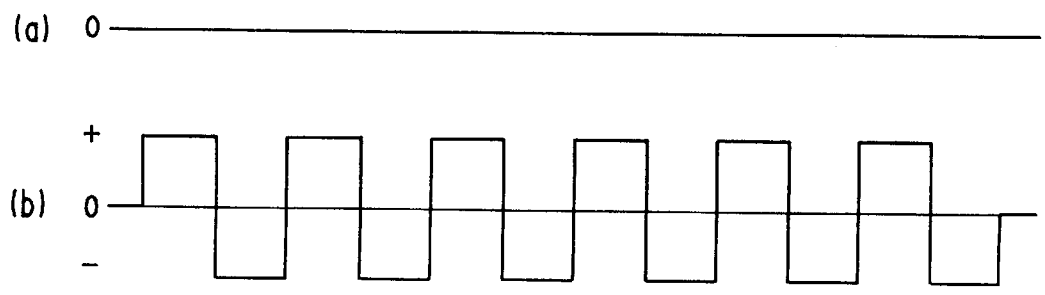
FIG. 5 is a diagram showing the phases of the contact portions of second therapeutic fingers during tapping massage by the second fingers, (a) showing the phase of the contact portions of first therapeutic fingers, (b) showing the phase of the contact portion of the second finger, the plus side of (b) representing the movement of the second finger contact portion toward an affected part pressing direction, the minus side of (b) representing the movement of the same in a direction away from the affected part.

FIG. 5 shows the phases of the contact portions 70, 71 in the case where the back 19 of the user 15 is massaged by tapping with the second finger 48, with the first finger 46 in contact with the upper part or the upper to front part of the shoulder 18 of the user 15 to prevent the upper part of the user's body from moving upward or forward.

Figure 6:
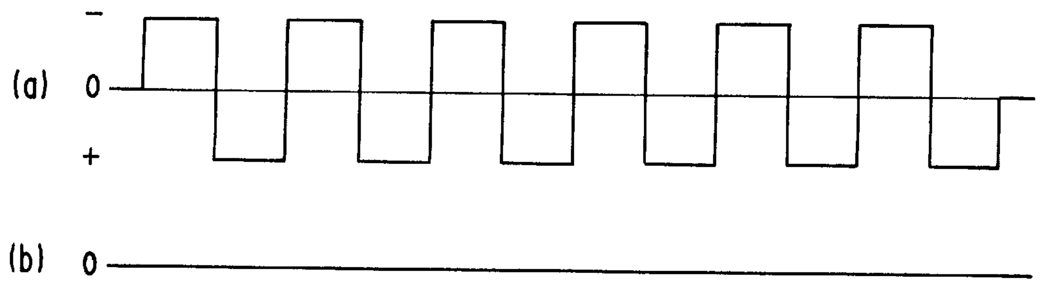
FIG. 6 is a diagram showing the phases of the contact portions of the first therapeutic fingers during tapping massage by the first fingers, (a) showing the phase of the contact portion of the first therapeutic finger, (b) showing the phase of the contact portion of the second finger, the plus side of (a) representing the movement of the first finger contact portion toward an affected part pressing direction, the minus side of (a) representing the movement of the same in a direction away from the affected part.

FIG. 6 shows the phases of the contact portions in the case where the upper part or the upper to front part of the user's shoulder 18 is tapped with first finger 46 for massage, with the second finger 48 in contact with the back 19 of the user 15 to prevent the upper part of the user's body from moving rearward.

Figure 7:
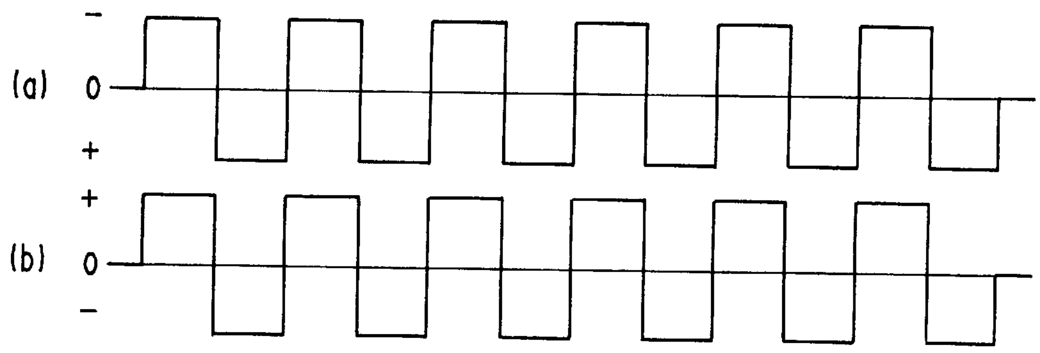
FIG. 7 is a diagram showing the phases of the contact portions of the first and second therapeutic fingers as moved alternately for tapping massage, (a) showing the phase of the contact portion of the first therapeutic finger, (b) showing the phase of the contact portion of the second finger, the plus side of (a) and (b) representing the movement of the contact portion toward an affected part pressing direction, the minus side thereof representing the movement of the same in a direction away from the affected part.

FIG. 7 shows the phases of contact portions 70, 71 in the case where the shoulder 18 and the back 19 of the user 15 are tapped for massage alternately with the first finger 46 and the second finger 48. In this case, when the first finger 46 moves out of contact with the shoulder 18, the second finger 48 taps the back 19; conversely, when the second finger 48 leaves the back 19, the first finger 46 taps the shoulder 18.

Figure 8:
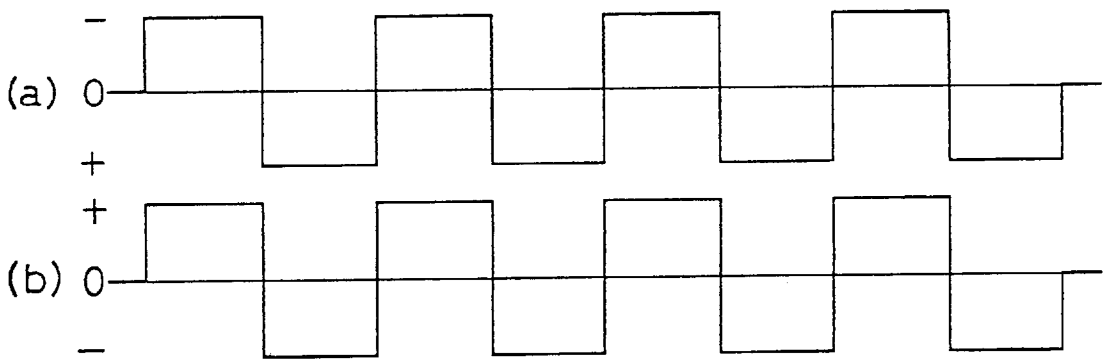
FIG. 8 is a diagram showing the phases of the contact portions of the first and second therapeutic fingers as moved alternately for finger-pressure massage, (a) showing the phase of the contact portion of the first therapeutic finger, (b) showing the phase of the contact portion of the second finger, the plus side of (a) and (b) representing the movement of the contact portion toward an affected part pressing direction, the minus side thereof representing the movement of the same in a direction away from the affected part.

FIG. 8 shows a case wherein the tapping period of FIG. 7 is lengthened. The massage thus given is more similar to finger-pressure massage than the tapping massage of FIG. 7.

Figure 9:
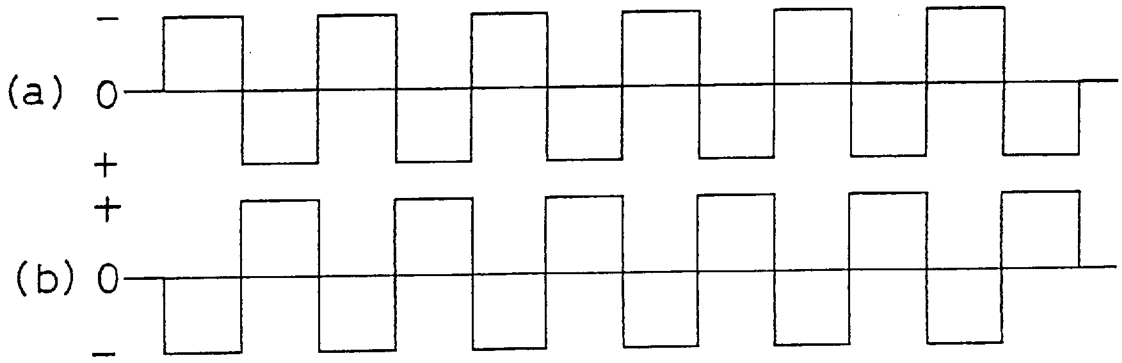
FIG. 9 is a diagram showing the phases of the contact portions of the first and second therapeutic fingers as moved simultaneously for tapping massage, (a) showing the phase of the contact portion of the first therapeutic finger, (b) showing the phase of the contact portion of the second finger, the plus side of (a) and (b) representing the movement of the contact portion toward an affected part pressing direction, the minus side thereof representing the movement of the same in a direction away from the affected part.

FIG. 9 shows the phases of the contact portions 70, 71 in the case where the shoulder 18 and the back 19 of the user 15 are massaged by tapping these parts simultaneously with the first finger 46 and the second finger 48. This operation is shorter in period than the usual kneading massage operation.

At least two massage operations can be performed alternately using a change-over switch (not shown) or the like. Alternatively, a massage may be given with the fingers of the right and left massage units 10, 11 matched to each other or reversed in movement.

When the contact portions 70, 71 of FIGS. 5 to 7 and FIG. 9 are driven at a frequency of several Hz to about 10 Hz, the most effective tapping massage is given. It is desirable that the operation of FIG. 8 resembling finger-pressure massage be effected slightly more slowly.

While the massage machine 12 of the chair type is an embodiment of the invention, the invention can of course be embodied as a handy massage device. The backrest of the chair-type massage machine has two massage units of the invention as arranged side by side, whereas only one massage unit may be used.

Since a wide variety of massages can be given by driving the therapeutic fingers 46, 48 and holding the finger at rest, the affected part will not feel painful or becomes insensitive, or the user is unlikely to become tired of massage.

When one of the therapeutic finger is held at rest, the upper part of the user's body can be prevented from moving, with the other finger giving an effective tapping massage to the affected part of the user 15.

The shoulders 18 of the user 15 can be massaged more effectively if the guide rails 20, 20 are so bent that the upper part or the upper to front part of the shoulder 18 can be tapped with the contact portion 70 of each first finger 46.

Embodiment 2

Figure 10:
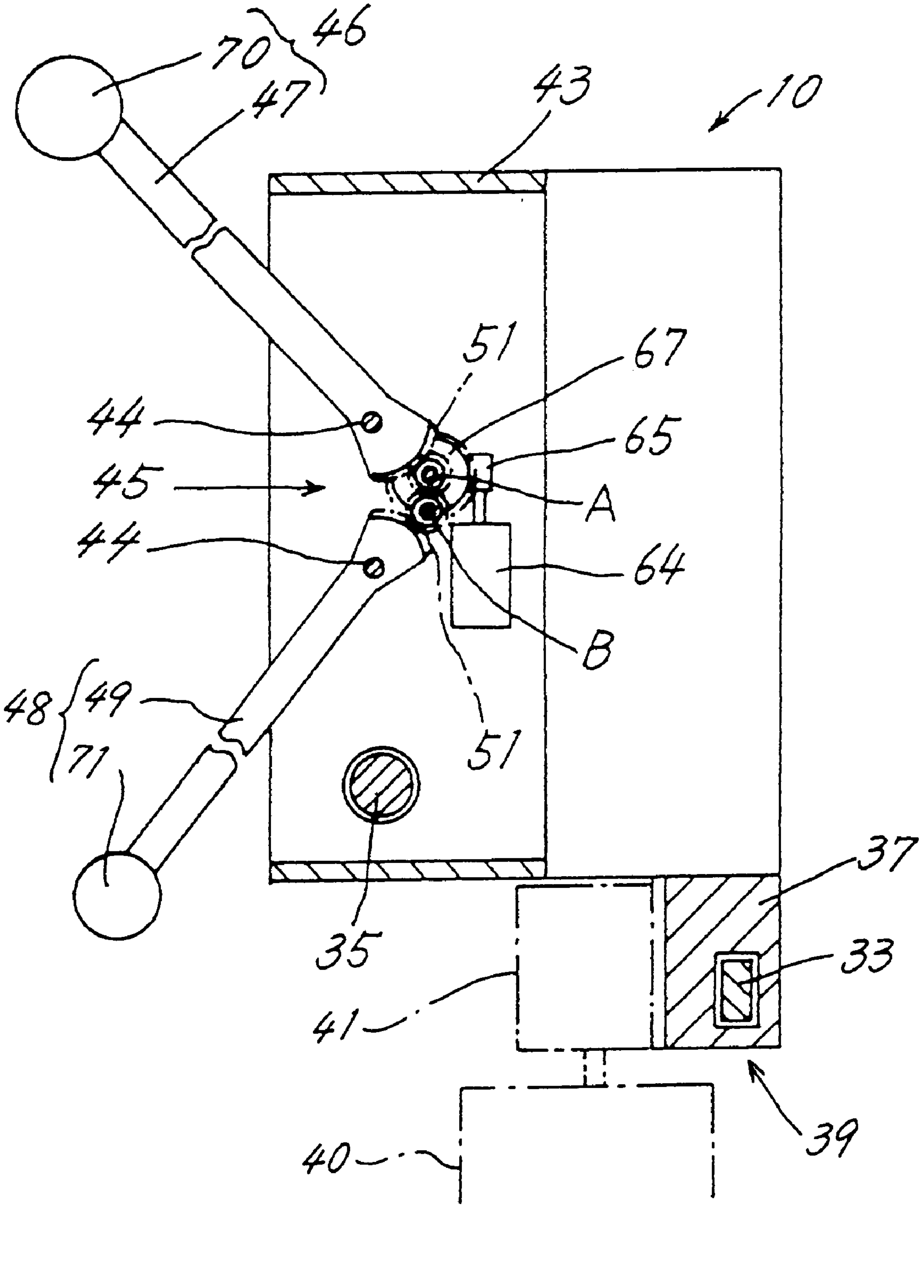
FIG. 10 is a view showing a different embodiment of the invention and corresponding to a view in section taken along the line B—B in FIG. 3 of the massage unit.

This embodiment has the same construction as Embodiment 1 except that the massage units 10, 11 are different as shown in FIG. 10, and therefore will not be described except the different feature.

A casing 43 houses one finger drive assembly 45 for pivotally moving two therapeutic fingers 46, 48 in a vertical plane. The drive assembly 45 comprises a finger drive motor 64. The drive shaft of the motor 64 carries a worm 65 which is in mesh with a worm wheel 67 supported by the casing 43 with a shaft. The worm wheel 67 is integral with an intermediate gear A, which is in mesh with a sector gear 51 of an upper arm 47. The intermediate gear A is also in mesh with an intermediate gear B supported by the casing 43 with a shaft. The intermediate gear B is in mesh with a sector gear 51 of a lower arm 49.

When the finger drive motor 64 is driven with the direction of rotation changed over from forward to reverse and vice versa at a predetermined time interval, the fingers 46, 48 are pivotally moved, each about its pivot, toward and away from each other by means of the gears.

The left massage unit 11 has the same construction as the right massage unit 10. The casing 43 of the unit 11 has its bottom secured to the upper side of a left rack 38.

The massage machine 12 of the foregoing construction operates in the modes to be described below.

Strong Massage

Figure 11:
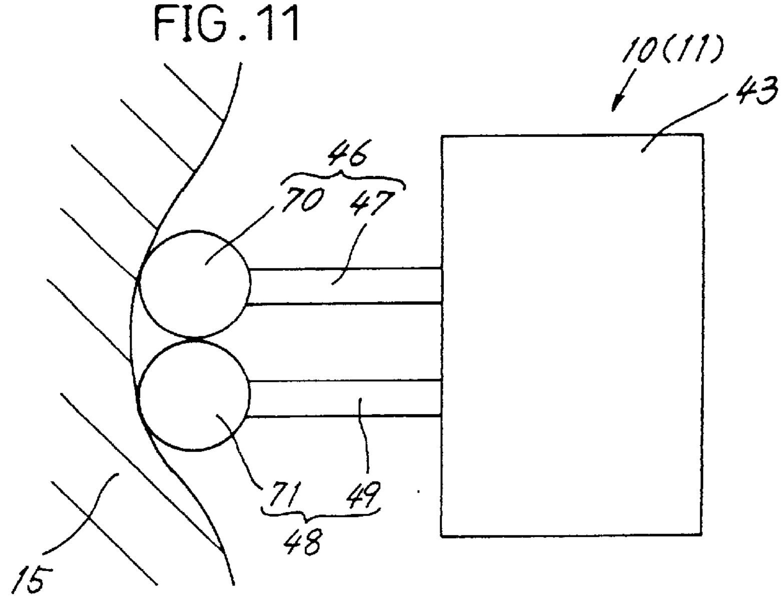
FIG. 11 is a diagram showing the massage unit in operation for a somewhat strong massage, with the upper and lower contact portions held in contact.

The finger drive motor 64 of each of the massage units 10, 11 is driven to bring the upper and lower contact portions 70, 71 into contact with each other. A strong massage can be given since the pressure to be applied to the user 15 by each massage unit 10 (11) is concentrated on one spot as seen in FIG. 11.

With the upper and lower contact portions 70, 71 held in contact with each other, the motor 40 for moving the massage units 10, 11 toward or away from each other is driven with the direction of rotation changed repeatedly to move the units 10, 11 toward and away from each other sideways, whereby a somewhat strong massage can be given.

When the chain drive motor 29 is driven forward and reversely with the upper and lower contact portions 70, 71 held in contact, the massage units 10, 11 move up and down along the guide rails 20, 20, whereby the muscles of the back can be stretched somewhat intensively.

Soft Massage

Figure 12:
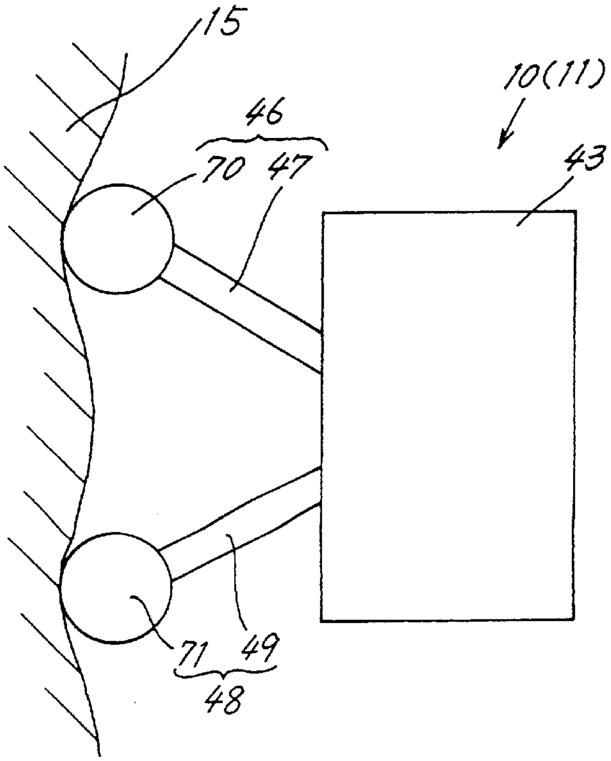
FIG. 12 is a diagram showing the massage unit in operation for a soft massage, with the upper and lower contact portions spaced apart.
Figure 13:
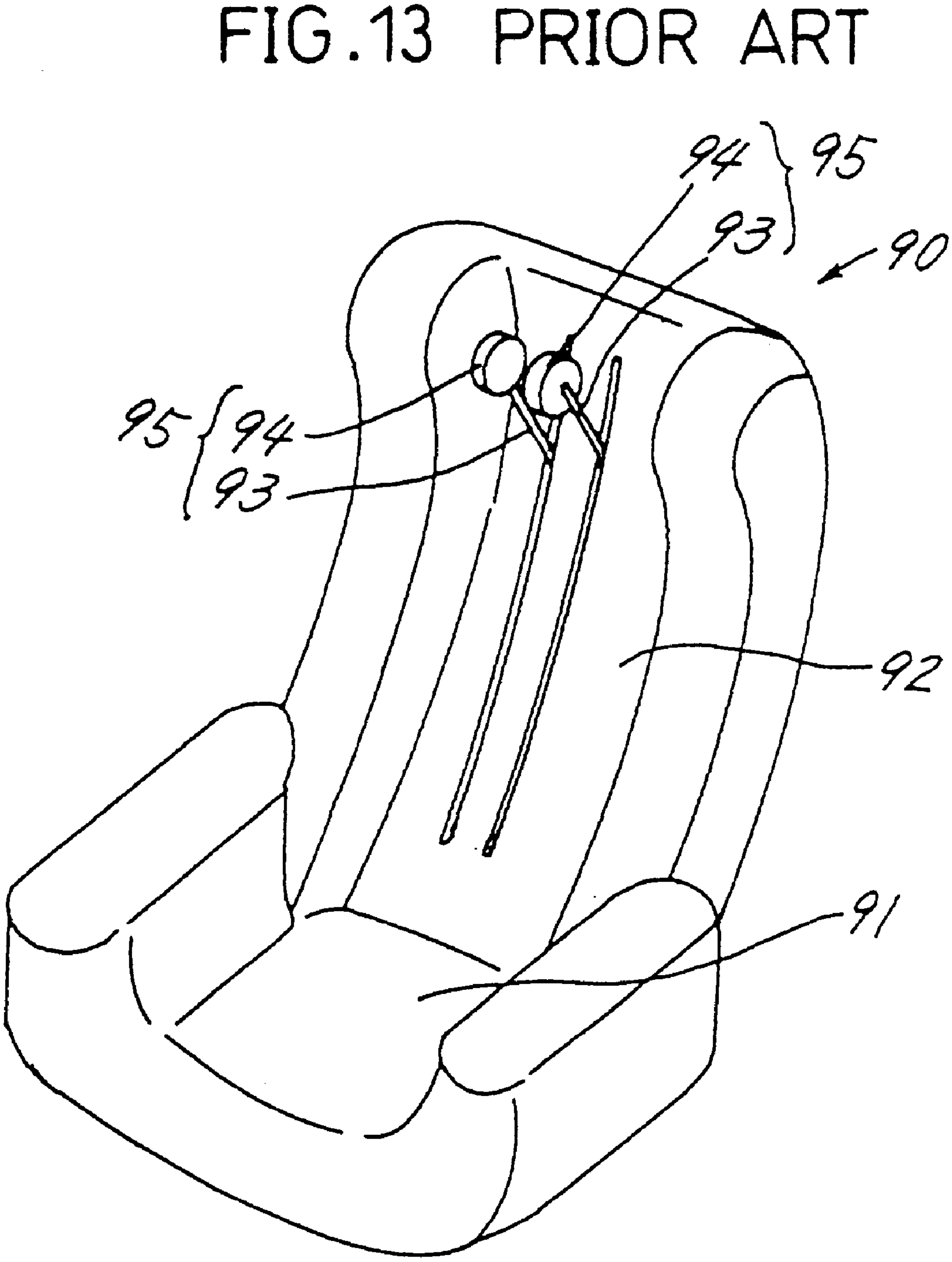
FIG. 13 PRIOR ART
FIG. 13 is a perspective view of a conventional massage machine of the chair type.

The upper and lower contact portions 70, 71 of each of the massage units 10, 11 are spaced apart by driving the finger drive motor 64. The distance between the contact portions 70, 71 is determined by the user 15. As shown in FIG. 12, the pressure to be applied by the massage unit 10 (11) is dividedly applied to two spots to give a weak or soft massage.

A soft lateral kneading or back muscle stretching massage can be given by driving the motor 40 or chain drive motor 29 forward and reversely, with the upper and lower contact portions 70, 71 held spaced apart.

With the massage machine 12 of the present invention, concentrated pressure can be applied to the affected part of the user 15 for somewhat strong massage, by moving the contact portions 70, 71 of upper and lower fingers 46, 48 of the massage units 10, 11 along the affected part while holding the contact portions 70, 71 of each unit in contact with each other. Further when the upper and lower contact portions 70, 71 are spaced apart, the pressure to be applied to the affected part acts dividedly, whereby somewhat weak massage can be given. Whether the contact portions 70, 71 are to be held in contact or spaced apart can be determined as desired by the user 15, so that the user 15 can be massaged with the desired intensity.

Apparently, the present invention can be altered or modified by one skilled in the art without departing from the spirit of the invention. Such modifications or alterations are included within the scope of the invention as set forth in the appended claims.

What is claimed is:

1. A massage machine adapted to be disposed in a chair, said massage machine comprising:

at least one massage unit adapted to be disposed in a backrest of the chair, the massage unit having upper and lower therapeutic fingers arranged one above the other in a substantially vertical plane and projecting forwardly of the backrest, each of the therapeutic fingers having a contact portion at a forward end of an arm, and each of the arms being coupled at a base end thereof to respective finger drive means operable independently of each other, the respective finger drive means each receiving a drive signal sequence different from each other, the upper and lower therapeutic fingers being individually pivotally moveable in the substantially vertical plane.

2. A massage machine as defined in claim 1 wherein a contact portion at a forward end of the upper therapeutic finger is moveable to a position permitting the contact portion to reach an area from an upper part to a frontal part of a shoulder of a user seated in the chair.

3. A massage unit comprising:

an upper therapeutic finger for giving a first tapping massage on an area from an upper part to a frontal part of a shoulder of a user; and a lower therapeutic finger for giving a second tapping massage on an area from a back to a posterior part of the shoulder of the user, the upper and lower therapeutic fingers being arranged in a substantially vertical plane, each of the upper and lower therapeutic fingers having a portion to be brought into contact with the user at a forward end of an arm, the arms being coupled to respective finger drive means operable independently of each other, the respective finger drive means each receiving a drive signal sequence different from each other, and the upper and lower therapeutic fingers being individually pivotally moveable in the substantially vertical plane.

4. A massage unit as defined in claim 3 wherein the first finger drive means and the second finger drive means are respectively a first finger drive motor and a second finger drive motor operable independently of each other, and the tapping massage is given to the user by one of the first and second therapeutic fingers by holding one of the first and second finger drive motors at rest with the contact portion in contact with the user and driving the other finger drive motor alone forward and reversely repeatedly.

5. A massage unit as defined in claim 3 wherein the first finger drive means and the second finger drive means are respectively a first finger drive motor and a second finger drive motor operable independently of each other, and the tapping massage is given to the user by controlling the first finger drive motor and the second finger drive motor so that when one of the therapeutic fingers moves toward the user, the other therapeutic finger moves away from the user.

* * * * *